(12) United States Patent
Pickens

(10) Patent No.: US 11,071,641 B2
(45) Date of Patent: Jul. 27, 2021

(54) OSTOMY PROTECTIVE DEVICE

(71) Applicant: Danielle Sturm Pickens, Montgomery, TX (US)

(72) Inventor: Danielle Sturm Pickens, Montgomery, TX (US)

( * ) Notice: Subject to any disclaimer, the term of this patent is extended or adjusted under 35 U.S.C. 154(b) by 553 days.

(21) Appl. No.: 15/628,681

(22) Filed: Jun. 21, 2017

(65) Prior Publication Data

US 2018/0369011 A1 Dec. 27, 2018

(51) Int. Cl.
*A61F 5/445* (2006.01)
*A61F 5/44* (2006.01)

(52) U.S. Cl.
CPC ............ *A61F 5/445* (2013.01); *A61F 5/4408* (2013.01)

(58) Field of Classification Search
CPC combination set(s) only.
See application file for complete search history.

(56) References Cited

U.S. PATENT DOCUMENTS

| | | | | |
|---|---|---|---|---|
| 1,922,763 | A * | 8/1933 | Gricks | A61F 5/445 604/340 |
| 2,129,054 | A * | 9/1938 | Geisler, Jr. | A61F 5/445 604/340 |
| 2,496,175 | A * | 1/1950 | Perry | A61F 5/445 604/335 |
| 2,549,649 | A * | 4/1951 | Van Hove | A61F 5/445 604/341 |
| 2,656,838 | A * | 10/1953 | McConnell | A61F 5/445 604/340 |
| 3,398,744 | A * | 8/1968 | Hooper | A61F 5/445 604/340 |
| 4,636,206 | A * | 1/1987 | Ederati | A61F 5/4404 604/340 |
| 4,723,952 | A * | 2/1988 | Esposito | A61F 5/448 604/338 |
| 4,867,749 | A * | 9/1989 | Steer | A61F 5/448 604/337 |
| 5,178,614 | A * | 1/1993 | McDowell | A61F 5/445 604/332 |
| 5,338,315 | A * | 8/1994 | Baker | A61F 5/445 128/888 |
| 5,653,701 | A * | 8/1997 | Millman | A61F 5/4408 604/337 |
| 8,316,985 | B2 * | 11/2012 | Bain | A61F 5/441 181/198 |
| 9,757,270 | B2 * | 9/2017 | Carrubba | A61F 5/448 604/337 |
| 9,907,689 | B2 * | 3/2018 | Persichina | A61F 5/4404 604/337 |
| 10,070,987 | B2 * | 9/2018 | Scott | A61F 5/4404 604/345 |

(Continued)

OTHER PUBLICATIONS https://www.stomaprotector.com/product/stoma-protector-for-two-piece-bag/.

*Primary Examiner* — Guy K Townsend
(74) *Attorney, Agent, or Firm* — R. William Graham

(57) ABSTRACT

A device for use by a person who has undergone an ostomy includes a protective housing having at least one outer surface, the housing having a pair of laterally extending surfaces connected to the outer surface to form a cavity for receiving the about an external aid proximate the flesh opening. The device also includes a belt receiving surface which is formed in the outer surface.

6 Claims, 5 Drawing Sheets

(56) References Cited

U.S. PATENT DOCUMENTS

| | | | |
|---|---|---|---|
| 10,258,495 B2* | 4/2019 | Luce | A61F 5/449 |
| | | | 604/345 |
| 2009/0182191 A1* | 7/2009 | Redlich | A61F 5/445 |
| | | | 600/32 |
| 2014/0148771 A1* | 5/2014 | Luce | A61F 5/445 |
| | | | 604/345 |
| 2014/0276500 A1* | 9/2014 | Scott | A61F 5/4404 |
| | | | 604/343 |
| 2014/0276519 A1* | 9/2014 | Luce | A61F 13/02 |
| | | | 604/378 |
| 2014/0276526 A1* | 9/2014 | Luce | A61F 13/02 |
| | | | 604/393 |
| 2014/0324002 A1* | 10/2014 | Luce | A61F 5/448 |
| | | | 604/338 |
| 2015/0088081 A1* | 3/2015 | Hakel | A61F 5/445 |
| | | | 604/337 |
| 2016/0113810 A1* | 4/2016 | Hanuka | A61F 5/4401 |
| | | | 604/333 |
| 2017/0128254 A1* | 5/2017 | Persichina | A61F 5/4404 |
| | | | 604/337 |
| 2017/0231802 A1* | 8/2017 | Luce | A61F 5/441 |
| | | | 604/335 |
| 2018/0369011 A1* | 12/2018 | Pickens | A61F 5/445 |
| | | | 604/345 |
| 2019/0321213 A1* | 10/2019 | Morrison, Sr. | A61F 5/445 |
| | | | 604/337 |

* cited by examiner

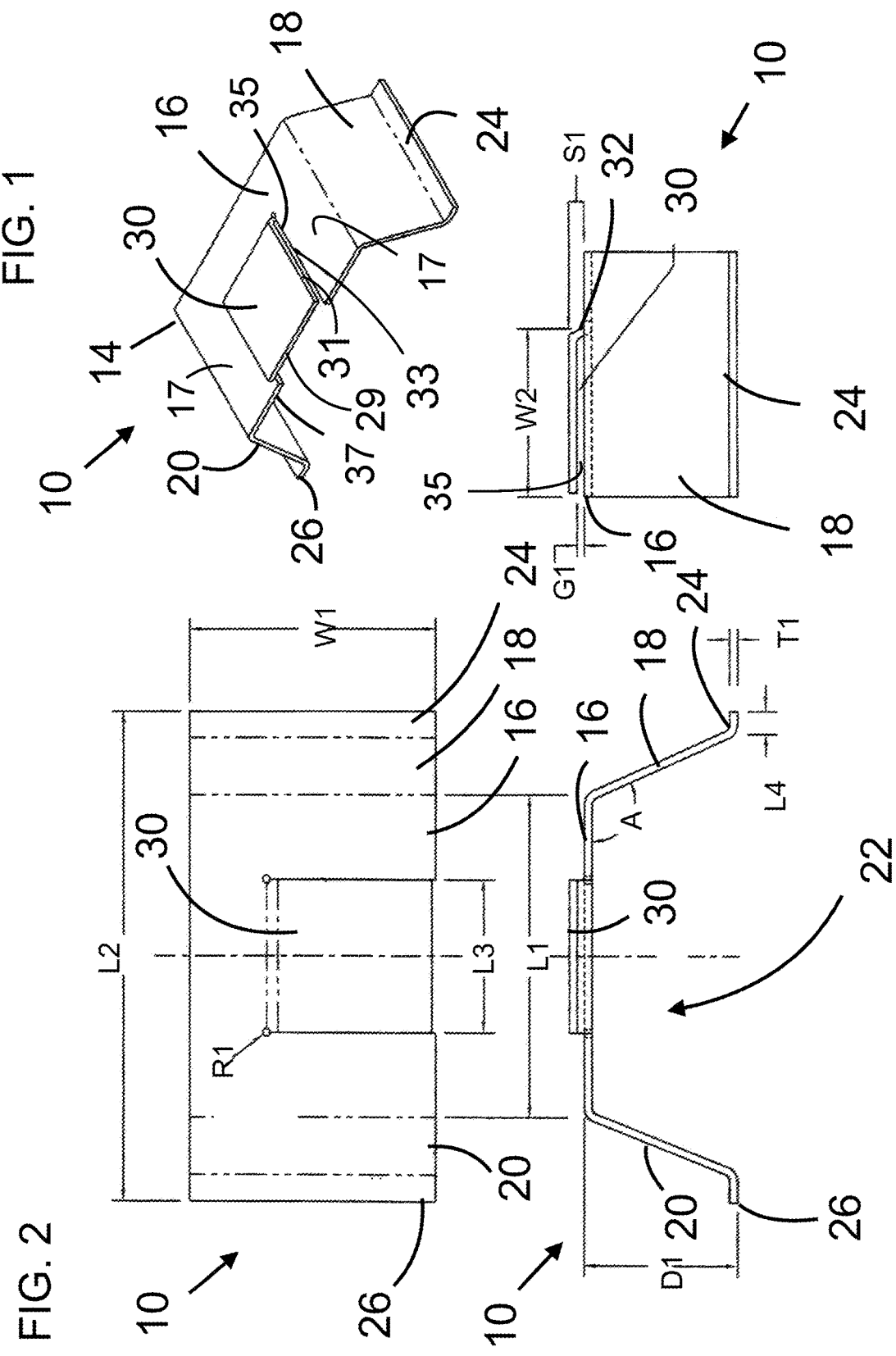

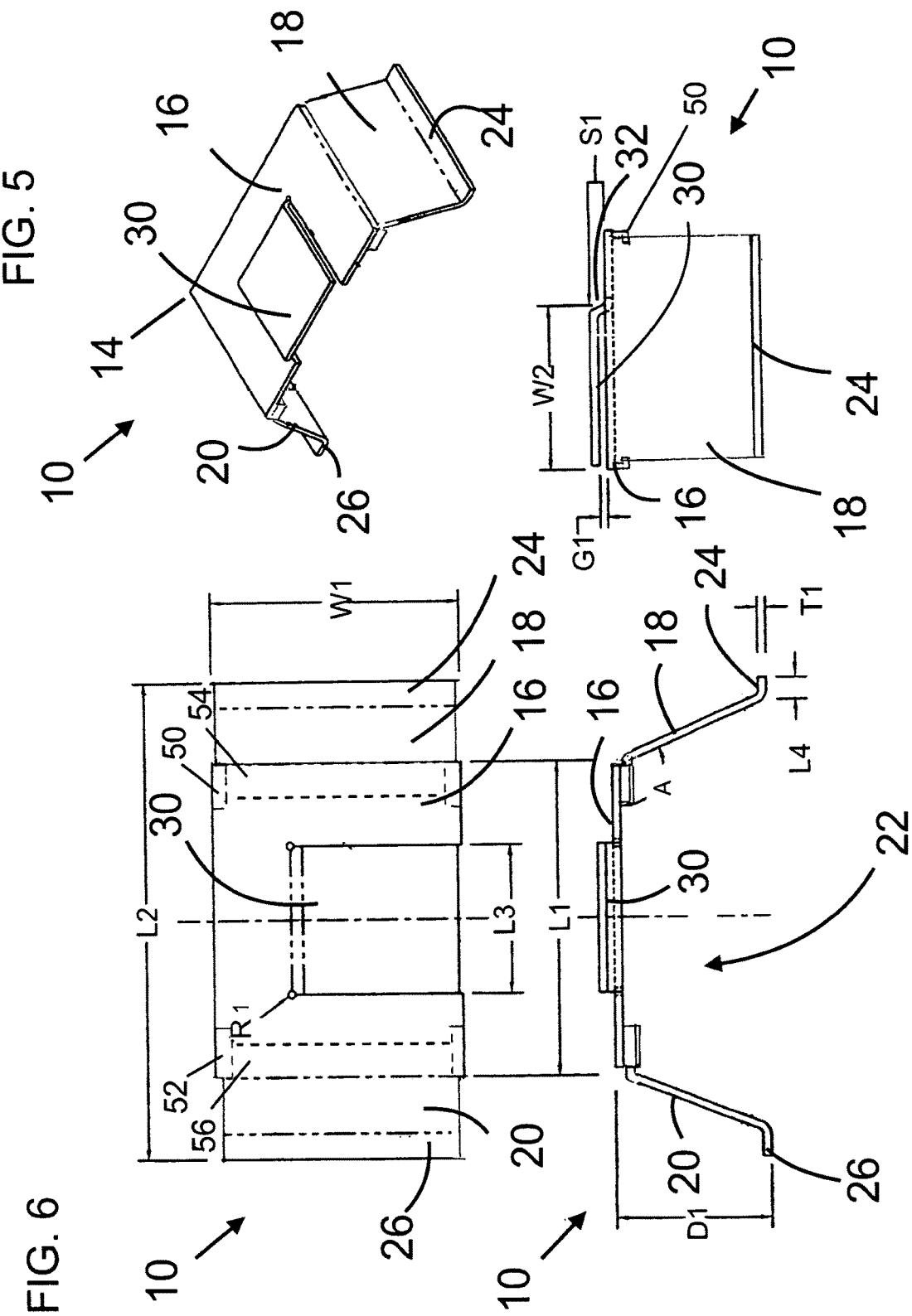

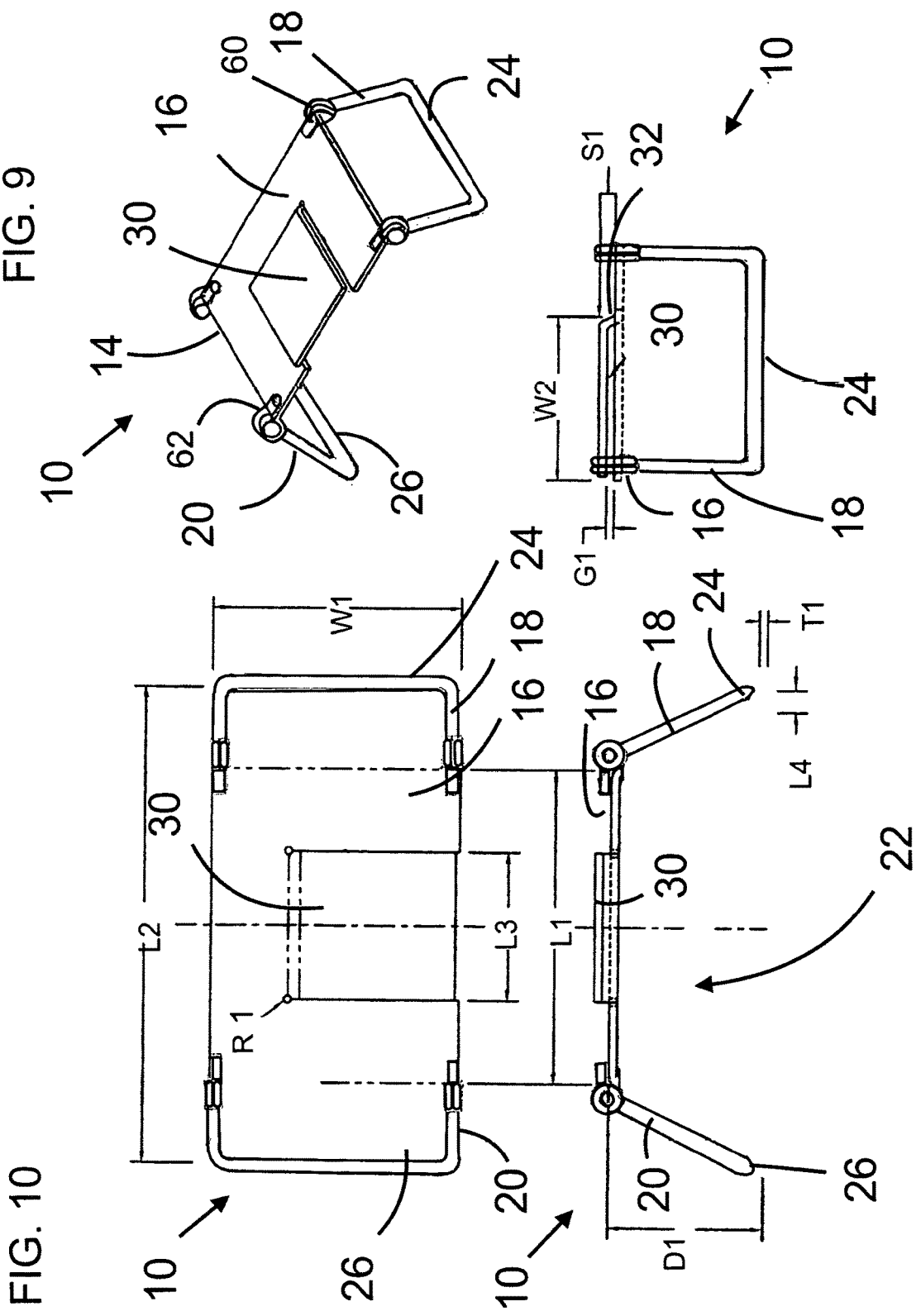

OSTOMY PROTECTIVE DEVICE

BACKGROUND OF THE INVENTION

Field of Invention

The instant invention relates to the field ostomy procedures and devices worn as a result of such procedures. More particularly, the invention relates to a device for aiding a patient who has undergone an ostomy procedure.

Prior Art

There exist methods and devices for use by people who have an artificial opening in an organ of the body created during an operation such as a colostomy, ileostomy, or gastrostomy, for example. Such prior devices basically encompass the artificial opening and associated medical aids extending from the opening. The prior protectors are typically of a rigid material and held in place by wrap or elastic band in an effort to keep the device in place. These prior devices can be difficult to use in a attempting to perform daily routines which require walking and driving and where it is desirable to have some range of movement.

There remains a need to improve stoma protective devices and the mobility of the wearer. This instant invention solves the prior problems in the art.

SUMMARY OF INVENTION

It is an object to improve the treatment of people undergoing an ostomy procedure.

Another object is to provide a device which aids a person having undergone an ostomy procedure.

Still another object is to provide more user friendly protective device for a person having a stoma protecting the stoma from pressure and impact, preventing leaks from the adhesive flange of a stoma pouch, and preventing pancaking of medical aids.

The instant invention provides a unique design which employs flexible or movable sides and a slotted surface to removable receive a belt, particularly a seat belt. This device is comfortable for the user to wear in performing various activities including but not limited to driving a vehicle.

Accordingly, one aspect of the invention is directed to a device for use by a person who has undergone a ostomy and is subject to having a flesh opening through which a medical tube extends which can connect for example to a bag for the treated condition together which are referred to as an "external aid." An embodiment of the device includes a protective housing having at least one outer surface, a pair of laterally extending surfaces connected to the outer surface and extending in a common direction relative to the outer surface to form a cavity for receiving about the external aid proximate the flesh opening. The device also includes a belt receiving surface which is formed in a preferred embodiment as an integral part of the the outer surface, wherein the belt receiving surface extends generally parallel to the outer surface in a spaced relation thereto and connects at one end to the outer surface. The laterally extending surfaces can be integrally connected to the outer surface, or removably connected and can be fixed, pivotally or hinged thereto. The laterally extending surfaces are preferably designed to permit flexibility of movement of the outer surface relative the wearer's body surface.

BRIEF DESCRIPTION OF THE DRAWINGS

FIG. 1 shows a perspective view of an embodiment of the invention.

FIG. 2 shows a top view of the embodiment of FIG. 1.

FIG. 3 shows an end view of the embodiment of FIG. 1.

FIG. 4 shows a side view of the embodiment of FIG. 1.

FIG. 5 shows a perspective view of another embodiment of the invention.

FIG. 6 shows a top view of the embodiment of FIG. 5.

FIG. 7 shows an end view of the embodiment of FIG. 5.

FIG. 8 shows a side view of the embodiment of FIG. 5.

FIG. 9 shows a perspective view of yet another embodiment of the invention.

FIG. 10 shows a top view of the embodiment of FIG. 9.

FIG. 11 shows an end view of the embodiment of FIG. 9.

FIG. 12 shows a side view of the embodiment of FIG. 9.

DETAILED DESCRIPTION OF THE INVENTION

Figure 13:
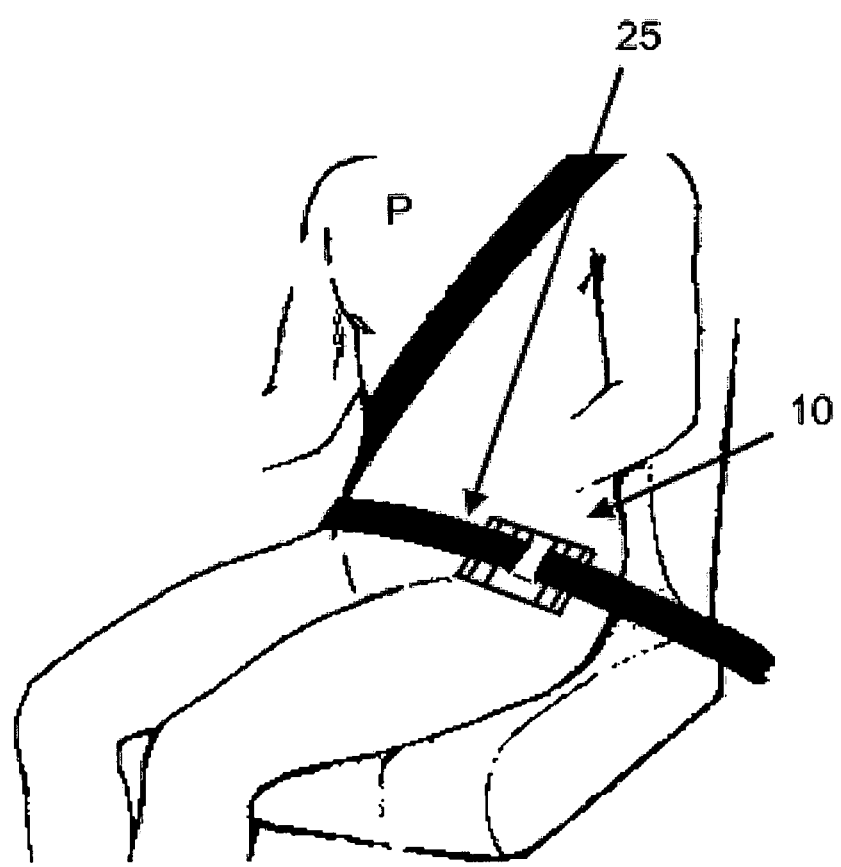
FIG. 13 shows a perspective view of an embodiment of the invention in use.

Referring now to the drawings, the device for use by a person P who has undergone an ostomy is generally referred to by the numeral 10. Like numbers refer to like parts throughout the specification. The device 10 can be formed of metal or plastic and can be integral single component or comprised of multiple connected components.

As discussed, the person P who has undergone a ostomy is subject to having a flesh opening O through (e.g., stoma) which a tube T may extend and here is shown to connect to a bag B for the condition together which are referred to as "external aid 12." An embodiment of the device 10 includes a protective housing 14 having at least one outer surface 16 which can be of a suitable size and configuration, here shown as a rectangular configuration having an exemplary length L1 of about 5-6 inches with an over all length L2 of about 8 inches and a width W1 of about 4 inches. The housing 14 has a pair of laterally extending surfaces 18 and 20 connected to the outer surface 16 and extending in a common direction relative to the outer surface 16 to form a cavity 22 for receiving the about the external aid 12 proximate and the flesh opening O. By way of example in FIG. 1, the laterally extending surfaces 18 and 20 extend at an obtuse angle A of about 115 degrees, though it is recognized other angles may work to carry out the invention and thus providing a relaxed depth D1, for example, 2.5 inch, of the device 10. The laterally extending surfaces 18 and 20 can include feet or flanged ends 24 and 26 having a length L4 for example about 0.5 inch. By virtue of the material make-up, thickness which impart its flexibility, and angle formed between components, when feet 24 and 26 are disposed on the person P, and pressure is applied on the outer surface 16 by belt 25, for example, the feet 24 and 26 and laterally extending surfaces 18 and 20 are free to move enabling the outer surface 16 to change relative lateral position to the person P and thus depth D1 varies with pressure applied to outer surface 16. As will be understood by reading the disclosure hereinafter, this provides a more comfortable experience to the user.

The device 10 includes a belt receiving surface 30 which is formed in a preferred embodiment as an integral part of the housing 14 and is an outermost disposed part of the housing 14, wherein the belt receiving surface 30 extends generally parallel to the outer surface 16 in a spaced relation to more inwardly disposed adjacent outer portions 17 of the outer surface 16 having a gap therebetween. The belt receiving surface 30 has a free outer edge 29 connecting to side edges 31 which are next to edges 33 of the adjacent outer portions 17 defining a slotted area 35 at a gap G1, for example ⅛ inch, to receive a belt therethrough and between the belt receiving surface 30 and adjacent outer portions 17 of the outer surface 16. The belt receiving surface 30 spans a width W2, e.g. 2.5 inches and connects at one end 32 to the outer surface 16 thereby providing a surface differential S1. A radius R1 can be provided at the connection to aid against stress fractures. Also, edges 31 and 33 can be smoothed to provide ease of use and minimize injury. Slots 35 between edge 31 and 33 extend from and an outer edge 37 inwardly to permit receipt and removal of the belt through the outer edge 37. The laterally extending surfaces 18 and 20 can be integrally connected to the outer surface 16 in the case of making the same from a single sheet material or from a single mold. FIG. 1 is representative of this type embodiment.

Figure 14:
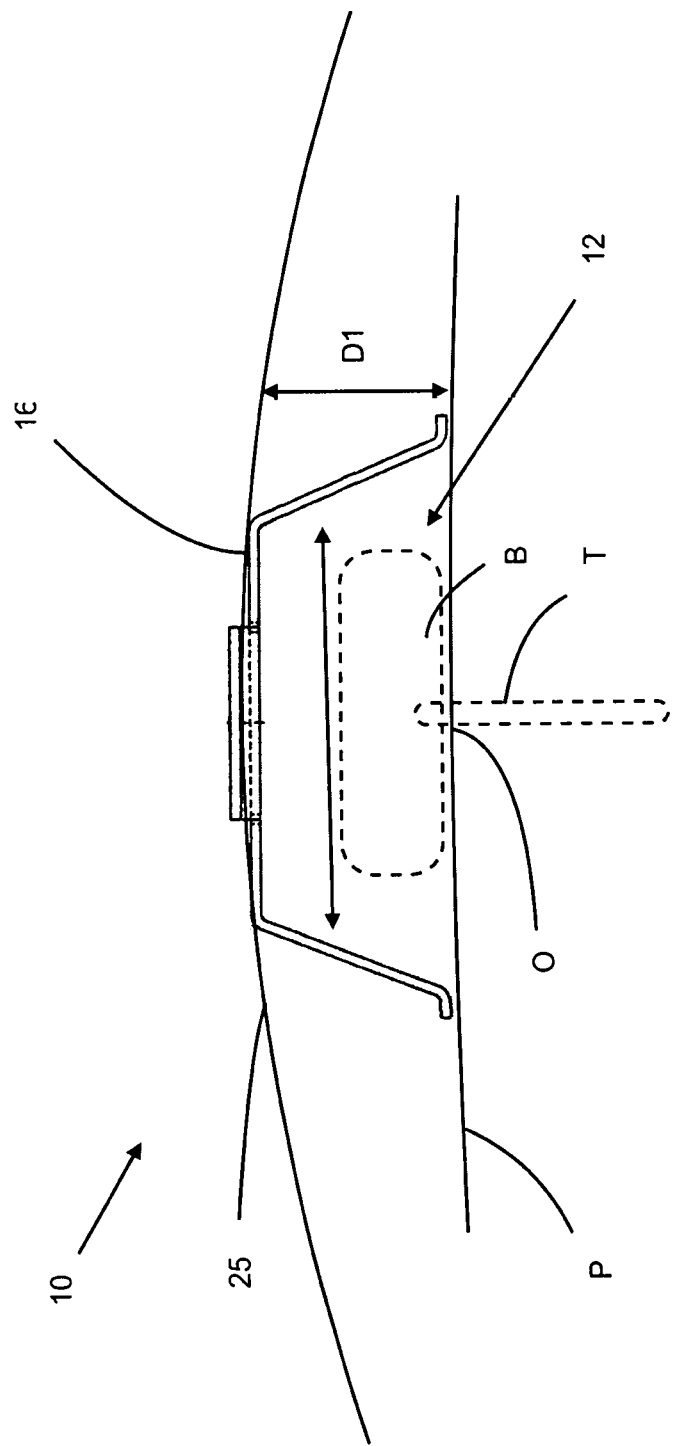
FIG. 14 illustrates another view of an embodiment of the invention in use.

Optionally, the laterally extending surfaces 18 and 20 can be removably connected as illustrated in FIGS. 5-12 and can be made to be fixed in a position or pivotally or hinged to the outer housing 16. The laterally extending surfaces 18 and 20 are preferably designed to permit flexibility of movement of the outer surface 16 relative the wearer's body B. As illustrated in FIGS. 13 and 14, the device 10 is particularly useful in applications where the user is requiring seat belt 25 be worn, such as in a car, plane or other vehicle so requiring. Prior heretofore, the seat belt 25 would pose a difficulty to the person P as it would either be placed around or over the protective device and in either case it would cause interference with the normal operation of prior protective devices or discomfort to the user. However, with the instant invention, the device 10 removably receives the seat belt 25 in the belt receiving surface 30. Embodiment in FIGS. 5-8 employ slide channels 50 and 52 to receive an upper end flange 54 and 56. The embodiment of FIG. 9-12 shows a pivotal or hinged connections 60 and 62. By virtue of the flexibility of positioning the outer surface 16 as understood above, the outer surface 16 can be adjusted relative to the person's body to maintain the protective function of the external aid 12 reducing the incidences of tube and bag collapsing and restricting the flow of the matter into the stoma pouch when pressure is exerted on it while providing the user greater comfort in changing the profile device 10.

It is to be understood that numerous additions, modifications, and derivations may be made to the present invention which fall within the intended scope of the above description and the claims appended hereto should be afforded the scope of such additions, modifications, and derivations. It will be appreciated the dimensions which are set forth above may be such as to carry out the intended purpose of the invention. The configuration and construction materials used in connection with the invention may be modified or changed so long as the intended functionality is neither degraded nor destroyed.

What is claimed is:

1. A device for use by a person who has undergone an ostomy and is subject to having a flesh opening through which an external aid extends and which is adapted for use with a seat belt, which includes:
    a protective housing having at least one outer surface, said housing having a pair of laterally extending surfaces connected to said outer surface and extending at an obtuse angle and in a common direction relative to first outer portions of said outer surface to form a cavity therebetween for receiving about the external aid proximate the flesh opening, and a belt receiving surface integrally formed on said housing and being outwardly disposed relative to said first outer portions, wherein the belt receiving surface extends generally parallel to said outer surface in a spaced relation to said first outer portions of said outer surface having a gap therebetween, said belt receiving surface having a free outer edge connecting to side edges of said belt receiving surface which are adjacent edges of said first outer portions and define a slotted area to receive a seatbelt thereby and therethrough and said slotted area between said edges extend from said free outer edge inwardly to points where said side edges integrally join said outer surface adjacent first outer portions to permit receipt and removal of the seatbelt thereby and therethrough.

2. The device of claim 1, wherein said laterally extending support surfaces are integrally connected to said outer surface.

3. The device of claim 1, wherein said laterally extending support surfaces are pivotally removably connected to said outer surface.

4. The device of claim 1, wherein said laterally extending support surfaces are one of fixed, pivotally or hinged connected to permit flexibility of movement of said outer surface relative a person's body surface.

5. The device of claim 1, wherein said housing and lateral extending support surfaces are made of a material to permit flexibility of movement of said laterally extending surfaces relative to said outer surface and change of depth of the cavity formed between said outer surface and said laterally extending support surfaces.

6. The device of claim 1, wherein said edges are smoothed to provide ease of use and minimize injury.

* * * * *